United States Patent [19]

Ellis et al.

[11] Patent Number: 4,770,657
[45] Date of Patent: Sep. 13, 1988

[54] THREE-DIMENSIONAL SHAPED FEMININE PAD WITH ABSORBENT IN THE ELASTICIZED EDGES

[75] Inventors: Louise C. Ellis, Appleton; Julie T. Basten, Green Bay; Allan J. Krueger, Winneconne; Russell L. Nowak, Green Bay, all of Wis.

[73] Assignee: Kimberly-Clark Corporation, Neenah, Wis.

[21] Appl. No.: 868,927

[22] Filed: May 28, 1986

[51] Int. Cl.⁴ .............................................. A61F 13/18
[52] U.S. Cl. ............................ 604/385 A; 604/385 R; 604/370
[58] Field of Search ............... 604/358, 385 A, 385 R, 604/366, 370, 379

[56] References Cited

U.S. PATENT DOCUMENTS

| | | | |
|---|---|---|---|
| 2,064,431 | 12/1936 | Jurgensen | 604/385 R |
| 4,195,634 | 4/1980 | DiSalvo et al. | 604/385.1 |
| 4,205,679 | 6/1980 | Repke et al. | 604/379 |
| 4,425,129 | 1/1984 | Karami | 604/385 |
| 4,433,972 | 2/1984 | Malfitano | 604/385 |
| 4,534,769 | 8/1985 | DeJonckheere et al. | 604/369 |
| 4,552,795 | 11/1985 | Hansen et al. | 604/358 |
| 4,579,556 | 4/1986 | McFarland | 604/385 A |
| 4,601,678 | 9/1986 | Weisman et al. | 604/368 |
| 4,639,254 | 1/1987 | LeGault et al. | 604/385 |
| 4,668,230 | 5/1987 | Damico et al. | 604/385 A |
| 4,701,177 | 10/1987 | Ellis et al. | 604/385 A |

FOREIGN PATENT DOCUMENTS

| | | |
|---|---|---|
| 5037485 | 11/1985 | Australia . |
| 1206301 | 6/1986 | Canada . |
| 0040447 | 11/1981 | European Pat. Off. . |
| 0098512 | 3/1984 | European Pat. Off. . |
| 0091412 | 10/1985 | European Pat. Off. . |
| 0164435 | 1/1986 | European Pat. Off. . |
| 0183668 | 6/1986 | European Pat. Off. . |
| 0238053 | 9/1987 | European Pat. Off. . |
| 2142242 | 1/1985 | United Kingdom . |
| 2156681 | 10/1985 | United Kingdom . |
| 2168253 | 6/1986 | United Kingdom . |

Primary Examiner—Stephen C. Pellegrino
Assistant Examiner—Denise Whelton
Attorney, Agent, or Firm—Paul A. Leipold

[57] ABSTRACT

The invention is generally accomplished by providing a curved elongated absorbent pad for absorption of bodily excretions comprising a liquid-impermeable backing member, an upper reinforcing absorbent member, a reservoir absorbent member, and liquid-permeable body-side member. The upper reinforcing absorbent member is provided as a sheet below the permeable cover and extends substantially coextensively with the backing member at the edges of said pad. The lower absorbent reservoir member is shaped generally in a manner as to have an hourglass or dog-bone shape that provides a narrower middle portion of soft absorbent material. The middle portion of the lower absorbent, also in the preferred embodiment, is somewhat thicker than the reservoir absorbent portions at the ends of the pad. The pad is provided with upstanding side portions in the middle of each long edge in the area where the lower soft absorbent is narrower. The upper reinforcing absorbent sheet extends into the side edges. The preferred feminine pad further is curved so as to generally conform to the pudendum in the front and extend to about the area of the anus in the rear.

29 Claims, 5 Drawing Sheets

THREE-DIMENSIONAL SHAPED FEMININE PAD WITH ABSORBENT IN THE ELASTICIZED EDGES

TECHNICAL FIELD

This invention relates to absorbent pads for external application. It more particularly relates to an elongated cup-shaped garment particularly adapted for menstrual use as a catamenial device.

BACKGROUND ART

The present invention relates to an absorbent product, such as a sanitary napkin, comprising an absorbent body and a jacket enclosing said body, said jacket comprising a fluid-permeable layer located closest to the user when in use and a fluid-impermeable layer disposed on the opposite side—the back—of the absorbent body.

Leakage to the side has been a problem when using sanitary napkins. This has been a problem in all types of sanitary napkins, both the older types, i.e. thick and wide napkins, and in more modern types, e.g. so-called body-shaped napkins, which vary in thickness along their lengths and are relatively narrow in the midsection where they are thickest.

Sanitary napkins of the older, uniformly thick types are often greatly deformed when used quite simply because they are too large and not fitted to the shape of the human body. They also are not resilient and deform as the body of the wearer moves. Usually they are pressed together in the middle and bent along a longitudinal axis so that the front, the side in contact with the user, becomes convex with portions of the fluid-permeable layer facing out towards the sides at the same time as the fluid-impermeable back layer is more or less folded up resulting in a reduction in effective fluid-stopping surface. This means that fluid from the napkins can leak out through the folded out fluid-permeable front layer on both sides of the folded-up fluid-impermeable back layer. Leakage also is caused by the folding and shifting movement of the pad.

Attempts have been made to solve this problem by making the modern sanitary napkins so that when used they more closely follow the shape of the body and have their greatest absorption capacity where the need is greatest.

The modern sanitary napkins are not deformed especially much during use and are more comfortable. However, side leakage is still a substantial problem even in body-shaped napkins. On occasions when fluid discharge is great, experience has shown that not all the fluid has time to be absorbed; rather a portion can still leak out to the sides and over the longitudinal edges of the napkin.

Developments of the last few years, however, have made the napkins thinner and thinner. This has been made possible both by compressing the absorbent material, and by using high-absorbent material. Examples of such very thin and comfortable napkins are the thin sanitary pads with highly absorbent materials instead of sanitary napkins of the older thicker types.

For such thin napkins, side leakage is a problem as pads do not conform to the body. Since they are usually very thin, they must be relatively broad even in the middle, making them liable to be greatly deformed when used, unfortunately often resulting in edge leakage in this type of napkin as well.

Many different attempts have been made to eliminate the occurrence of lateral leakage. In thin napkins one example is to arrange a number of longitudinal compressed areas in the absorbent body for the purpose of rapidly spreading the fluid longitudinally. These compressed areas are, however, far from sufficient to satisfactorily eliminate edge leakage.

It is also known to further widen the fluid-impermeable back layer so as to cover, in addition to the back and side edges of the napkin, also a portion of the front side in contact with the user during use. In such a design the fluid already collected in the absorbent body is to be sure effectively enclosed, but instead there is the substantial disadvantage that the fluid-impermeable back layer folded in over the front side can cover a major portion of the napkin side facing the user when the napkin is deformed when used, whereby menstrual fluid can run directly out of the napkin on top of the portions of the back layer folded in over the front.

There have been proposed shaped pads for use as catamenial devices or incontinence use. European Patent application No. 0091412—Widlund discloses a shaped pad. The pad of Widlund has elastic along the edges of the center portion of a generally rectangular pad. The elastic serves to shape the pad into a bowed shape with the elasticized edges extending upward beside the absorbent portion. Great Britain Patent application No. 2,142,541—Buell discloses an elasticized waste containment garment, designed for incontinence use. This garment also has elasticized edges. In the Buell application the elastic extends almost the full length of the garment, and the elasticized edge portion not containing absorbent appears to be somewhat wider than that of Widlund. Other pads exhibiting elasticized edges are disclosed in UK No. 2,143,115—Damico and European No. 0,167,931—Damico et al. A feminine pad with elasticized edges is disclosed in United Kingdom Pat. No. 2,156,681—Mokry.

There remains a need for a pad that fits the curve of the human body, will remain stationary during use, is comfortable to wear, effective, particularly against side leakage, and discreet. Thinner rectangular pads of the prior art are not of a shape that easily conforms to the body without bunching and being deformed. Therefore, there remains a need for an improved pad for catamenial use or for light incontinence use.

DISCLOSURE OF THE INVENTION

An object of this invention is to overcome disadvantages of prior body-conforming absorbent pads.

An additional object of this invention is to provide catamenial devices with improved protection against side leakage.

A further object of this invention is to provide a pad that is comfortable to wear and stays in place while worn.

A further additional object is to provide a fitted catamenial pad that resists deformation while being worn.

These and other objects of the invention are generally accomplished by providing a curved elongated absorbent pad for absorption of bodily excretions comprising a liquid-impermeable backing member, an upper reinforcing absorbent member, a lower soft absorbent member, and liquid-permeable body-side member. The upper reinforcing absorbent member is provided as a sheet below the permeable cover and extends substantially coextensively with the backing member at the edges of said pad. The lower absorbent reservoir member is shaped generally in a manner giving an hourglass or dog-bone shape that provides a narrower middle portion of soft absorbent material. The middle portion of the lower absorbent, also in the preferred embodiment, is somewhat thicker than the reservoir absorbent portions at the ends of the pad. The pad is provided with upstanding side portions in the middle of each long edge in the area where the lower soft absorbent is narrower. The upper reinforcing absorbent sheet extends into the side edges. The preferred feminine pad further is curved so as to generally conform to the pudendum in the front and extend to about the area of the anus in the rear.

The preferred form of the pad, for feminine care, is formed from an elongated generally-rectangular backing sheet, reinforcing absorbent sheet and body-side liner with elastic applied to the backing, reinforcing absorbent and liner in the area forming a flap outside of the narrowed portion of the hour-glass shaped lower soft absorbent. When the elastic is in relaxed (non-stretched) form, it draws the flaps upward such that they extend above the lower absorbent, and further shorten the pad causing the pad to curve.

MODES FOR CARRYING OUT THE INVENTION

The pad of the invention has numerous advantages over the prior art pads. The absorbent being less wide in the middle portion allows a better fit in the area of the vaginal opening while the wider end portions help to hold the pad in place as well as providing additional adsorption and preventing leakage. The preferred form of the invention with upstanding walls and a thicker portion in the center provides a pad with superior absorbency and a high resistance to leakage. Further, the pad with the upstanding absorbent walls next to a narrow thick soft absorbent is comfortable with good liquid-holding capacity. Another advantage is that the pad of the invention, while shaped, is formed from a backing material and body-side liner that has parallel sides, thereby minimizing difficulty and cost in the formation of the pad.

The utilization of a reinforcing absorbent member beneath the bodyside liner has several advantages. The main advantage is that the shape retention of the pad is improved. The pad with the reinforcing member beneath the bodyside liner has less bunching. Bunching is narrowing of the pad at the end. Further, the pad exhibits less twisting in use. Another advantage is that the distribution of menstrual fluid in the absorbent is improved. This improvement is even more noticeable if the reinforcing member is embossed to create channels for fluid distribution. The edges of the pad being absorbent are a final barrier to leakage if the fluid is not being absorbed into the soft lower absorbent member or the fluid running on the pad surface reaches the edges. The pad with the sheet reinforcing member below the bodyside liner has greater integrity and holds together better when wet. The sheet reinforcing absorbent member, when formed of coform, also has the advantage that it pulls fluid from the bodyside liner member to keep the bodyside liner drier. The reinforcing absorbent member immediately below the bodyside cover also results in the cover looking whiter as fluid is pulled from the cover. This results in a better appearing pad. The reservoir absorbent acts to pull or remove fluid from the reinforcing absorbent so that it is further removed from contact with the wearer. These and other advantages of this invention will be apparent from the detailed description below and the description of the drawings.

Figure 1:
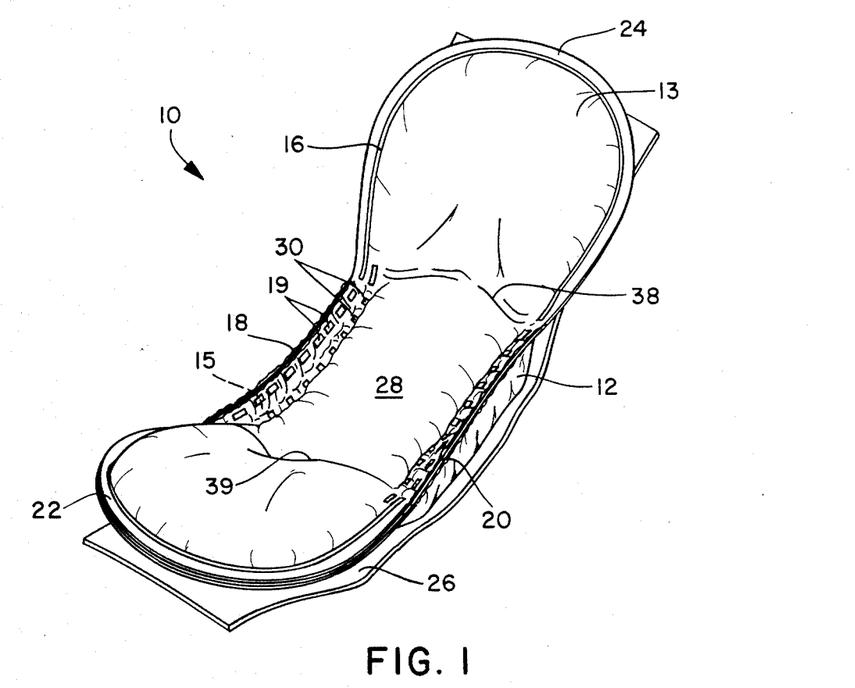
FIG. 1 is a perspective view of a pad in accordance with the invention.

As illustrated in FIG. 1, pad 10 is composed of a liquid-impermeable backing 12 that forms a basin shape. The body-side material 13 lines the interior of the basin. The reinforcing absorbent 15 is placed below the body-side member 13. The impermeable member 12 and body-side permeable member 13 are joined at a seal line 16 extending around the periphery of the ends 22 and 24 of pad 10. The walls 18 and 20 are sealed by dashed sealing lines 19 at their upper portion. The area where the wall meets the area of the pad containing the narrow lower reservoir absorbent 40 is sealed with dots or short dashes 30. Upstanding walls 18 and 20 are located in the middle portion of the long sides of the pad 10. The walls at their top are about the same distance apart as the width of the soft lower absorbent. The ends 22 and 24 are rounded. The pad is provided with a removable peel strip 26. The peel strip 26 may be removed to expose adhesive for attachment to an undergarment. The center portion 28 is somewhat raised up to about the height of the walls 18 and 20. The ends 22 and 24 are raised from the middle portion of the pad to form a bowed basin that will conform to the pudendum of a woman. The raised center portion 28 will generally be located near the vaginal orifice and urethral orifice.

Figure 2:
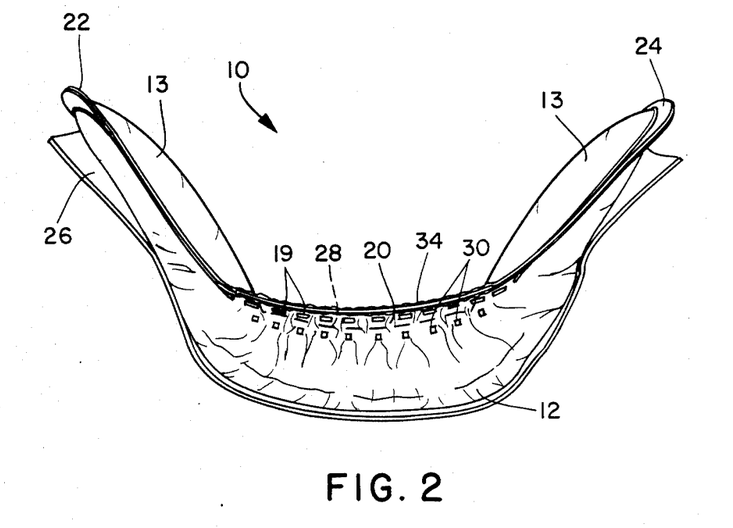
FIG. 2 is a side view of the pad of the invention.

FIG. 2 is a side view of the pad 10 of FIG. 1. The side view illustrates the peel strip 26 fastened to the bottom of basin 12. It also illustrates that the body side of the liner 13 is raised above the level of basin 12 at ends 22 and 24. Dashed seal line 30 is where the body-side liner 13, reinforcing absorbent 15 and basin 12 have been joined; the joining of the body-side liner and the basin may be accomplished in several ways, such as adhesively or by ultrasonics. The dotted or dashed seal line 19 extends as a continuous line to the ends (note numeral 16 in FIG. 1). It is noted that the raised center portion of the body-side lining 28 extends almost to the height of the top 34 of wall 20.

Figure 3:
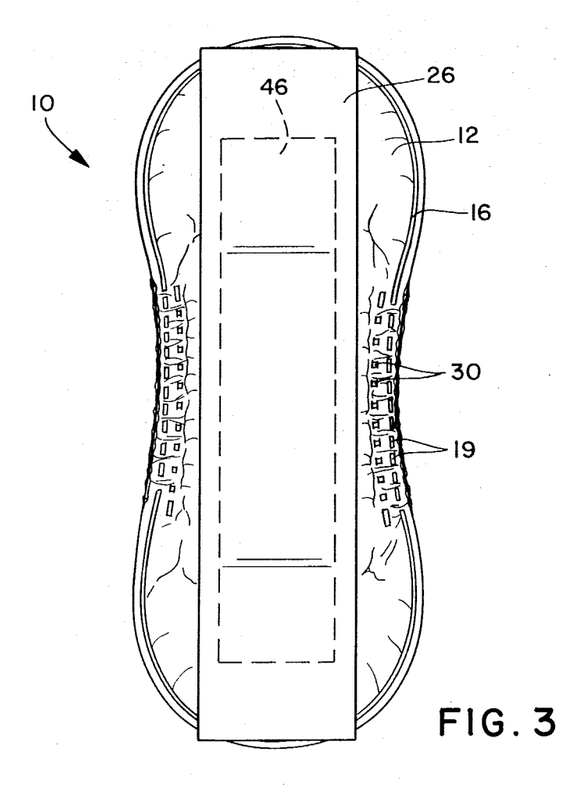
FIG. 3 is the bottom view of the pad of the invention.
Figure 4:
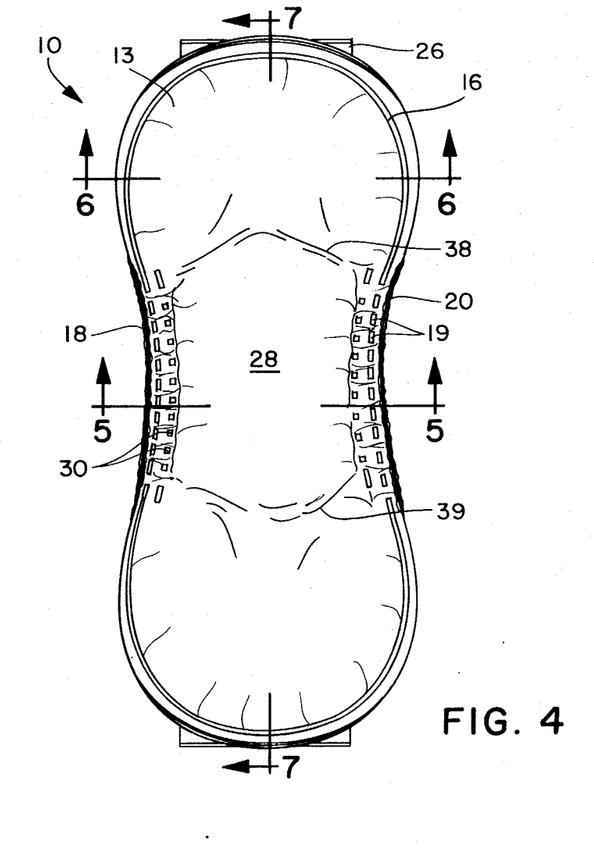
FIG. 4 is the top view of the pad of the invention.

FIG. 3 is a bottom view of the pad 10. The peel strip 26 covers the preferred single wide area of adhesive 46 or alternatively several lines of adhesive. FIG. 4 illustrates a top view of the pad of the invention. The pad is provided with a seal line 16 joining the liquid-impermeable backing 12 and the body-side liner 13 at the pad ends. The line 16 and dashed seal lines 19 and 30 are formed by ultrasonic sealing. However, the sealing areas may be formed by other methods such as heat sealing or adhesives. The pad has arcuate rugosities 38 and 39 where the ends of the pad turn up. However, the center portion 28 is generally smooth. The walls 18 and 20 flair slightly outward as they extend upward from the dashed seal line 30.

Figure 5:
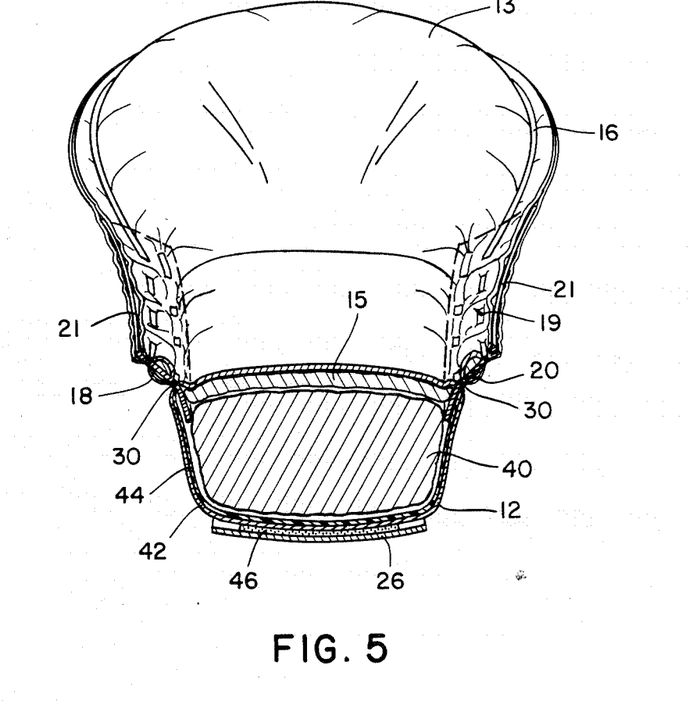
FIG. 5 is a section along line 5—5 of FIG. 4.
Figure 6:
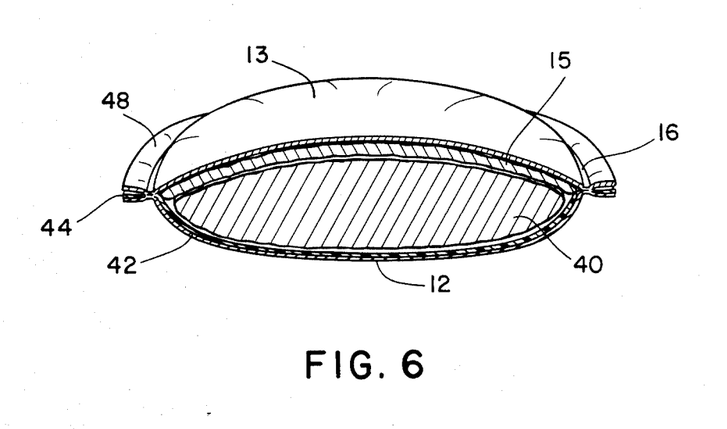
FIG. 6 is a section along line 6—6 of FIG. 4.
Figure 7:
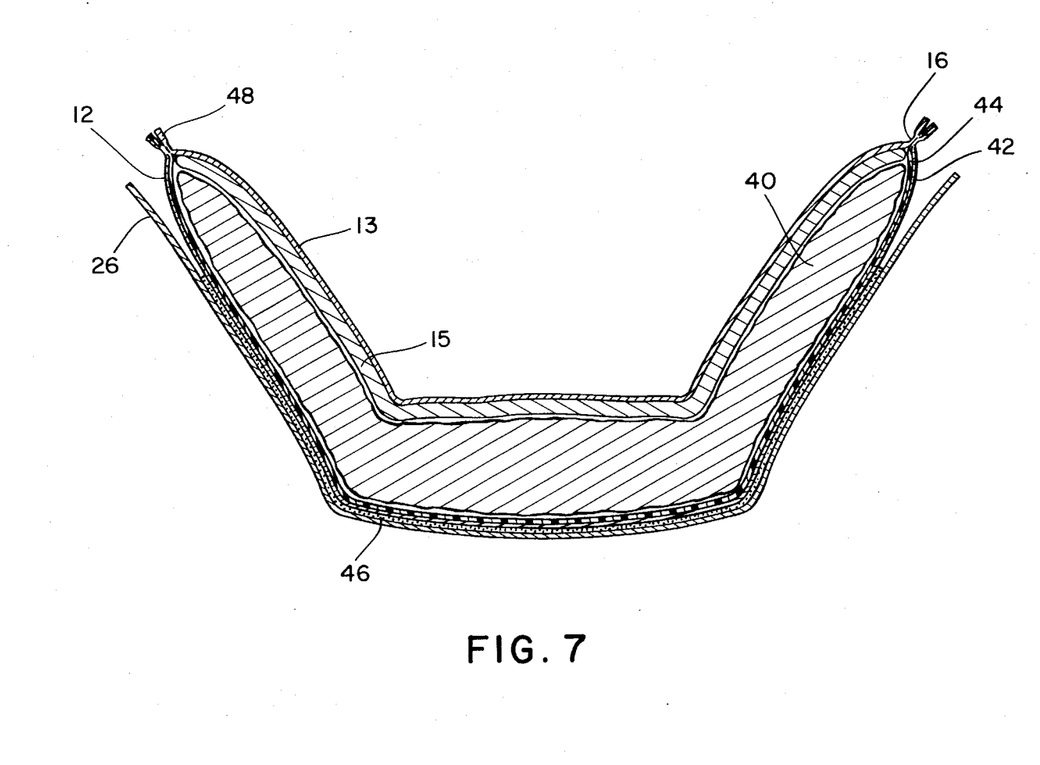
FIG. 7 is a cross-sectional view of the pad of the invention taken on line 7—7 of FIG. 4.

FIGS. 5, 6 and 7 are cross-sectional views of the pad taken on FIG. 4. FIG. 5 taken in the center portion of the pad across the width illustrates the reservoir absorbent 40 in the center portion of the pad forming an arched surface under permeable body-side layer 13. The walls 18 and 20 begin at dashed seal line 30 where the cover 13, elastic 21 and sheet of reinforcing absorbent 15 are bonded together and to the outer cover 12. Outer cover 12 is composed of two separate sheets formed into a single integral sheet 12. Sheet 12 is formed of a nonwoven outer sheet 42 and a liquid-impermeable polymer sheet 44 that are integrally connected. This provides a nonwoven outer surface that is soft and non-irritating to the skin. The peel strip 26 is located over adhesive 46 that is in a single wide area that will serve to hold the pad in place by bonding to the underwear of the wearer. FIG. 6 of a cross section taken at the wide portion near the end of pad 10 is somewhat wider than the center portion illustrated in FIG. 5. Further, the reservoir absorbent 40 is thinner than in the center portion and not as crowned or upwardly rounded. The view of FIG. 7 makes apparent the thicker middle portion of the pad's reservoir absorbents 40. The pad has the seal line 16 generally at about the vertical midportion of the absorbent 40. It is noted that the edges, such as 48, are loose and form a soft surface against the body.

Figure 8:
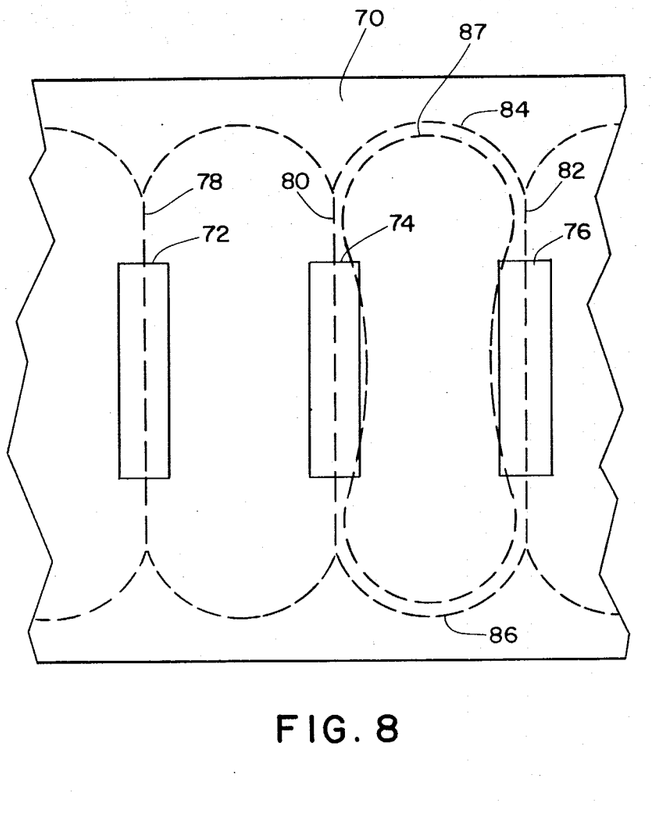
FIG. 8 illustrates a planar view of backing sheets of the invention with heat-shrinkable elastic in place.
Figure 9:
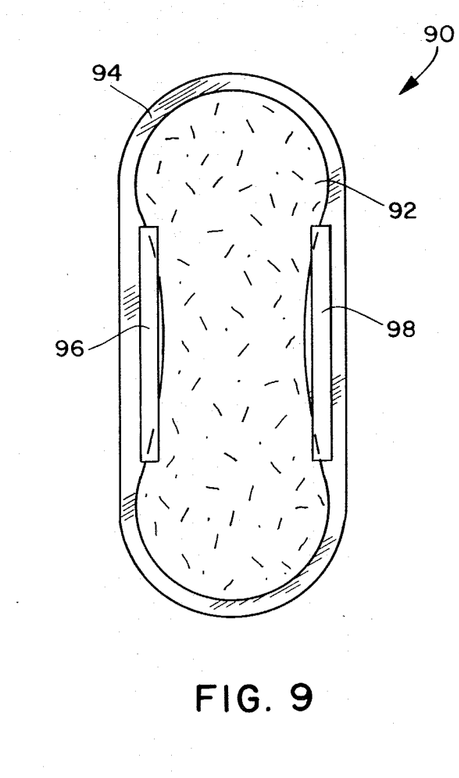
FIG. 9 illustrates in planar view another elastic placement system.

FIGS. 8 and 9 illustrate the formation of the products of the invention with two different optional placements of elastic material. In FIG. 8 a body-side sheet 70 is provided with several areas 72, 74 and 76 of material that will become elastic when it is heat shrunk. Lines 78, 80 and 82 represent cut lines between adjacent garments. The cut lines for the ends of the garments are represented by the lines 84 and 86. The heat-shrinkable material 72, 74 and 76 is nonelastic when applied to the backing material, but upon heating, shrinks and becomes elastic. Line 87 represents where the lower reservoir absorbent would be placed. It is preferred that the pad be folded with the ends overlapping prior to applying heat to the side edges to shrink the elastic. The elastic also may be shrunk by application of heat to the flat pad. It is preferred to fold the garment and shrink the elastic by application of heat from the sides as this allows better application of heated air to the pad. FIG. 9 illustrates an alternate elastic location in which a pad 90, having absorbent 92 on impermeable backing 94, has applied thereto elastic strips 96 and 98. These elastics may be adhesively connected to the backing or body side liner while under tension, or they also may be heat-shrinkable elastic film materials.

In other embodiments in accordance with the invention it is possible that a superabsorbent material could be added to the pad to increase the absorbence in certain areas without increasing the absorbent thickness.

The absorbent materials used in the instant invention may be any absorbent material that will absorb bodily exudates such as catamenial fluids or urine. Suitable for such use as the soft reservoir absorbent is wood fluff, rayon, cotton and meltblown polymer such as polyester or polypropylene or coform. Coform is a meltblown air-formed combination of meltblown polymer such as polypropylene with absorbent staple fibers such as cellulose. A particularly-preferred material has been found to be wood fluff as it is low in cost, relatively easy to form and has good absorbency. The absorbent may be formed in a single contoured layer such as illustrated in the drawings, or it may be formed in two stages with an extra layer added to a base layer in the center area where greater thickness was desired.

The outer liquid-impermeable covering may be any desired material. Typical of such materials are polymer sheets of polypropylene, polyethylene or combinations thereof. Particularly preferred are composite material of a polymer and a nonwoven fabric material. The composite sheets are generally formed by extrusion of the polymer onto the spunbonded web to form an integral sheet. This material is preferred as the outer fabric surface is not irritating to the skin of the wearer. The walls of the pad of the instant invention generally extend up into the crease between the legs and the pudendum of the wearer. Therefore, the outer wall portions may come in contact with the legs of the wearer and should provide a comfortable nonirritating feel.

The body-side material may be any suitable permeable member. Typical of such materials are nonwovens, tissues, perforated polymer sheets, and composites of these materials. A particularly-preferred body-side material has been found to be a composite of a spunbonded polypropylene web bonded to a layer of staple fibers of polyester or polypropylene. The bonding is in small areas of ultrasonic sealing. The cover is preferred as it has a cushioned feel. This material is described in U.S. Pat. No. 4,397,644—Mathews et al.

The reinforcing absorbent sheet beneath the bodyside liner may be any suitable material that will provide reinforcing for improved shape retention to the pad, as well as providing absorption in the upstanding edges. Further, the absorbent should not interfere with the adhering of the elastic, bodyside permeable member and impermeable backing member in the upstanding edge portions. A particularly preferred material is a layer of coform having a basis weight of between about 60 and about 120 grams per square meter. Coform is preferred as it is low in cost and has good wet strength properties and is sealable in the edge seals by heat or ultrasonics. The preferred materials further have a Gurley stiffness of about 1,000 to about 1,300 mg. as measured by a Gurley stiffness tester using TAPPI Test number T543—stiffness of paper (Gurley-type stiffness tester). The preferred stiffness gives resistance to deformation when worn, but is not so stiff that it will not conform to the body shape and cause discomfort to the wearer. The coform material further may in a particularly preferred form embossed so as to provide improved channels for liquid absorption and distribution on the pad.

The reinforcing absorbent sheet member in its most preferred form is designed to extend to a point just below the upper portion of the walls of the pad. The reinforcing absorbent 15 in the ends 13 of the pad may extend up to seal line 16 as illustrated in FIG. 6. On the other hand, it may extend through the seal line and to the outer edge to provide greater reinforcement. The sheet 15 in the preferred embodiment would extend to just below the upper dashed ultrasonic sealing line 19 in the all portion. This is illustrated in FIG. 5 where the coform sheet 15 extends above the intermittent sealing line 30 but just below the upper sealing line 19. By extending the reinforcing absorbent 15 to slightly below the seal line 19 rather than to the top of the wall, the pad has less tendency to leak at the edge as the reinforcing absorbent member 15 will not be exposed at the outer edge and therefore will not transfer fluid to the undergarments of the wearer. However, with absorbent being in the side walls, there is a tendency to transfer fluid back into the central absorbent members through the gaps in dashed line 30. This transfer is aided by the good fluid transfer properties of the preferred coform layer.

A preferred pad in accordance with this invention for catamenial use has a length between about 8½ and about 9½ inches with the elastic portion extended. The width is between about 2½ and about 3½ inches at the center and ends, respectively, when the elastic is extended. The lower soft absorbent member preferrably has a length between about 8¼ and about 8¾ inches with a middle width preferrably between about 1½ and about 1¾ inches. The width of the lower absorbent at the ends is between about 2¼ and about 2½ inches. The thickness of the soft lower absorbent in the middle is between about ½ and about ⅞ inch for a fluff member. The reinforcing sheet center width is about 2½ inches with the end width about 3 inches and a length of about 8¾ inches. A preferred basis weight for the preferred coform reinforcing sheet is about 65 to about 100 grams per square meter. The elastic length is between about 3½ and 4½ inches with a preferred length of about 4 inches. The elastic width is about ⅜ inches in each side.

The coform may be any suitable type. Coform is an air-formed mixture of meltblown fibers and staple fibers. In the most common and the preferred form, the meltblown fibers are polypropylene while the staple fibers are develicated wood fibers. A preferred blend is about 70 percent wood pulp and 30 percent polypropylene.

The use of the dot or dash ultrasonic sealing pattern at line 30 leaves access for fluid absorbed on the edges of the pad to be transferred to the central body of the pad between the sealed areas. Further, it allows shrinkage of the elastic at the edge of the fluff in an easier manner as the material can gather between the seal lines. A continuous line of sealing would inhibit shrinkage. The line of large dashes near the edge of the top of the elasticized walls help seal against leakage outward onto the clothing of the wearer, while the line of smaller dashes or dots closer to the fluff allow transfer of fluid into the central reservoir absorbent from the absorbent edge.

The gathered portion forming the wall of the pad may be formed by any of several means. The gathered portion at the side of the pad of the invention preferably is formed by the use of elastic. Any suitable elastic may be utilized. Heat-shrinkable elastics may find advantage in some formation methods in that the elastic may be applied in a nonelastic state as a film which becomes elastic upon heating. The heat-shrinkable material also has the advantage that it may be utilized on the entire flap with relative ease of formation. The material may be applied in a rectangular form, but when heating takes place from the body side of the pad, the absorbent will insulate any heat-shrinkable material from heat applied such that it will not shrink and only the area in the exposed flap will shrink. When normal elastics are utilized, the elastic generally is applied as an elongated strip that is glued in place while under tension and then allowed to relax. Such materials and processes for their application are well known in the art. Exemplary of heat shrinkable elastics are those of U.S. Pat. No. 3,912,565—Koch et al., U.S. Pat. No. 3,639,917—Althouse and U.S. Pat. No. 3,819,401—Massengale.

As an alternative embodiment, rather than the use of an impermeable polymer film backing with elastic to shape the pad, the pad of the invention may be formed from a moldable plastic foam material that is liquid impervious and soft to the wearer. The material would be molded with gathers in the raised wall portion so as to allow the pad to conform to the body of the wearer. Such a pad would not require elastic as it would be molded in the container shape rather than having the contraction of the elastic form the backing material into the desired shape. A suitable foam material is a polyethylene-polyvinyl-acetate foam that may be vacuum and thermally molded to shape and then has the absorbent and body-side liner placed therein.

In a third embodiment the gathers in the wall could be formed of heat shrinkage film without significant elastic properties. The pad would be formed in the same way as the heat shrinkable elastic containing preferred pad, but upon shrinking, the polymer would shape the pad but not provide elastic properties to the side walls.

The preferred catamenial pad of the invention is designed such that the wall portions extend into the crease at the sides of the female genital organs or pudendum. The length is designed so as to extend adequately, caudally and dorsally, to prevent leakage in those directions, while fitting to the body and not be uncomfortable or interfering with the fit of the clothes of the wearer. Although human body sizes and shapes come in a variety of forms, and it is possible to make an almost infinite number of garments to satisfy all body sizes, it has generally been found that a garment with a certain range of dimensions is satisfactory. Generally in the product of the invention the narrow width portion in the center of the long edges is between about 1½ and about 4 inches wide for catamenial and incontinence devices. Preferred for catamenial use is a width of about 2½ to 3½ inches for absorption without leakage. Generally the length of the pad measured on the longest dimension of the liquid-impermeable backing member is between about 6 and about 10 inches. A preferred length distance is between about 8½ and about 9½ inches for comfort and good leakage protection.

The adhesive to hold the garment in place may be placed upon the pad in any desired arrangement including a series of narrow strips. Generally the preferred arrangement is with the adhesive formed in one strip. The band has a total width of between about 1 and about 1½ inches and a length of about 4 to 6 inches.

The amount of lower reservoir absorbent and upper reinforcing sheet absorbents within the structure may be any suitable amount to absorb the fluids that are intended to be entrapped. Further, a highly-absorbent material, such as a hydrogel superabsorbent, may be added to the absorbent to aid in holding of fluid material.

The method of sealing the permeable member to the liquid-impermeable backing member may be any suitable method that does not leave a hard, uncomfortable residue that would be annoying to the wearer. Typical of sealing methods are heat sealing and adhesive sealing. The preferred method for the instant invention is ultrasonic sealing on a line inward of the edge of the pad at the ends, leaving a loose flap of material extending about a quarter inch outward from the seal line. Ultrasonic sealing is preferred as it results in a neat line with no adhesive cost and less tendency to perforate the material than heat sealing.

The preferred form for the lower reservoir absorbent of the invention is in an hourglass or dog-bone shape with a narrow portion in the middle. In the most preferred form, the soft fluff absorbent is thicker in the narrow portion to provide added absorbency in this critical area. When a pad with less absorbent properties is suitable, a single thickness layer of soft fluff absorbent may be utilized. The absorbent in the thick center portion is preferably between about 1.75 and about 3 times the thickness of the end portions. Alternatively a pad of generally uniform thickness may be utilized, but with a higher absorbency material in the center portion than at the ends. Higher absorbency without added thickness may be achieved by using fibers of greater absorbency or by adding superabsorbents.

There are several variations of the invention that could be utilized in forming pads in accordance with the instant invention. The pad could be provided with an impervious folded-over edge, particularly in the elastic area, to minimize side leakage. The curvature of the pad could be varied from that shown in order to vary the fit for different sized people. Another embodiment of the invention could involve a slit down the longitudinal centerline of the lower fluff layer in order to cause it to raise the center and create a path for liquid absorption. The pad of the invention could be varied in larger sizes for incontinence protection. Rather than the reinforced absorbent member being formed of coform, it would be possible that it could be formed of a meltblown material or of an absorbent rayon.

The ratio of absorbency between the reinforcing absorbent layer and the soft lower absorbent may be any combination that produces a desired pad. Generally when utilized with a coform reinforcing sheet and fluff absorbent, the ratio of absorbency between the two materials is about 1:1. The ultimate absorbency of the pad may be varied depending on the primary use. A pad for utilization as an incontinent garment might have a higher ultimate absorbency on the order of up to about 60 cc, whereas the smaller garment intended for use as catamenial device could have an ultimate absorbency of between about 40 and about 50 gms. menstrual fluid. A preferred amount of absorbency for a catamenial device would be between about 15 and about 25 gms. of menstrual fluid in order to provide a device not having excessive bulk but being effective for the normal menstrual flow.

While the device of the invention finds primary use as an incontinent or catamenial device, it is possible the device could find a utility as a dressing for injuries to the ear, elbow, knee or other body areas.

In describing the present invention, certain embodiments have been used for purposes of illustration; however, other embodiments or modifications within the spirit and scope of the invention will readily occur to those skilled in the art after reading of this disclosure. Also the center portion with raised walls could be used with a long incontinence pad of a loincloth type. For instance, the pad of the invention could be held in place by belts rather than an adhesive. Further, the pad could be held in place only by a tight garment rather than by adhesive strips. The invention is accordingly not to be limited to the specific embodiments illustrated but only in accordance with the appending claims.

We claim:

1. An elongated catamenial or mild incontinence pad curved to the body shape having relatively long sides and narrowed ends for absorption of bodily excretions comprising a liquid-impermeable backing member, a reservoir lower absorbent inner member, liquid-permeable body-side member and a layer of reinforcing absorbent means immediately beneath said body-side member functioning to prevent bunching and twisting when said pad is worn, wherein said lower reservoir absorbent has a narrow center portion shape, said backing member, said body-side member and said reinforcing absorbent extend beyond said reservoir absorbent and have side edges forming flaps in the areas where the narrow portion of the soft lower absorbent does not overlay said backing, said flaps being gathered thereby raising said flaps to form an absorbent wall on each side of the narrower portion of said reservoir absorbent wherein the gathering of said flaps to form said walls is by elastic contraction, said reinforcing absorbent extends into said flaps and covers said elastic, and said reinforcing layer has a Gurley stiffness of between about 1,000 and 1,300 mg.

2. The pad of claim 1 wherein said backing is adhered to said liner in the area of said liner adjacent said reservoir absorbent.

3. The pad of claim 1 wherein the distance between said walls is about the width of the widest part of said lower absorbent.

4. The pad of claim 1 wherein said absorbent in the center of said pad extends up to about the height of said walls and wherein said absorbent is thicker in the middle of said pad than at the ends.

5. The pad of claim 1 wherein said impermeable layer is a composite of a fibrous web and a polymer film.

6. The pad of claim 1 wherein said elastic is generally coextensive with the wall.

7. The pad of claim 2 wherein said liner and said impermeable backing extend beyond the area where they are adhered to form a soft fringe at the ends of said pad.

8. The pad of claim 1 wherein said lower absorbent has an hourglass shape.

9. The pad of claim 1 wherein said reinforcing absorbent has a dog-bone shape.

10. The pad of claim 1 comprising a feminine pad.

11. The pad of claim 1 comprising an incontinent pad.

12. The pad of claim 1 wherein the flap of said body-side member is generally coextensive with the flap of said backing member in the wall area.

13. The pad of claim 1 wherein the elasticized side edges are generally parallel.

14. The pad of claim 1 wherein said flaps extend upward from about the middle of vertical height of the thickest portion of said reservoir absorbent.

15. The pad of claim 1 wherein said elastic extends to the outer edge of said wall.

16. The pad of claim 1 wherein said reinforcing absorbent extends into said wall area and covers said elastic.

17. The pad of claim 1 wherein said liquid-impermeable backing member comprises a foam sheet.

18. The pad of claim 1 wherein said backing member, reinforcing absorbent, body-side member and said elastic are sealed together at discontinuous areas of said walls.

19. The pad of claim 18 wherein the seal areas comprise two discontinuous ultrasonic sealing lines.

20. The pad of claim 1 wherein said reinforcing absorbent has an hourglass shape.

21. An elongated catamenial or mild incontinence pad curved to the body shape having relatively long gathered sides and narrowed ends for absorption of bodily excretions comprising a liquid-impermeable backing member, a reservoir lower absorbent inner member, liquid-permeable body-side member and a layer of reinforcing absorbent means functioning to prevent bunching and twisting when said pad is worn immediately beneath said body-side member, wherein said lower reservoir absorbent has a narrow portion shape, said backing member, said body-side member and said reinforcing absorbent extend beyond said reservoir absorbent and have side edges forming flaps in the areas where the narrower portion of the soft lower absorbent does not overlay said backing, said flaps being gathered thereby raising said flaps to form an absorbent wall wherein the edges are gathered by heat shrinkage of a generally inelastic polymer film to form generally inelastic edges.

22. The pad of claim 21 wherein said absorbent in the center of said pad extends up to about the height of said walls.

23. The pad of claim 21 wherein said inelastic film is generally coextensive with the wall.

24. The pad of claim 21 comprising a feminine pad.

25. The pad of claim 21 comprising an incontinent pad.

26. The pad of claim 21 wherein the flap of said body-side member is generally coextensive with the flap of said backing member in the wall area and wherein said inelastic film is generally coextensive with said backing member in said wall area.

27. The pad of claim 21 wherein said reinforcing absorbent layer has a Gurley stiffness of between about 1,000 and about 1,300 mg.

28. The pad of claim 1 wherein said reinforcing absorbent is embossed to create channels for fluid distribution.

29. The pad of claim 21 wherein said reinforcing absorbent is embossed to create channels for fluid distribution.

* * * * *

UNITED STATES PATENT AND TRADEMARK OFFICE
CERTIFICATE OF CORRECTION

PATENT NO. : 4,770,657

DATED : September 13, 1988

INVENTOR(S) : Louise C. Ellis, Julie T. Basten, Allan J. Krueger and Russell L. Nowak It is certified that error appears in the above-identified patent and that said Letters Patent is hereby corrected as shown below:

Column 3, line 47, delete "adsorption" and substitute therefor --absorption--.

Column 6, line 58, delete "all" and substitute therefor --wall--.

Claim 1, Column 10, line 5, delete "narrow" and substitute therefor --narrower--.

Claim 1, Column 10, line 12, after the word "and" insert --about--.

Claim 21, Column 11, line 1, after the word "narrow" insert --center--.

Signed and Sealed this

Twenty-eighth Day of November 1989

*Attest:*

JEFFREY M. SAMUELS

*Attesting Officer*      *Acting Commissioner of Patents and Trademarks*